United States Patent
Hänni et al.

(10) Patent No.: US 6,689,594 B1
(45) Date of Patent: Feb. 10, 2004

(54) DEVICE FOR ORGANIC CELL CULTURE AND FOR STUDYING THEIR ELECTROPHYSIOLOGICAL ACTIVITY AND MEMBRANE USED IN SAID DEVICE

(76) Inventors: Claude Hänni, 80, rue de la Charrière, CH-2300 La Chaux-de-Fonds (CH); Luc Stoppini, 26, rue Carteret, CH-1202 Geneve (CH)

( * ) Notice: Subject to any disclaimer, the term of this patent is extended or adjusted under 35 U.S.C. 154(b) by 0 days.

(21) Appl. No.: 09/701,956
(22) PCT Filed: Jun. 4, 1999
(86) PCT No.: PCT/CH99/00243
    § 371 (c)(1),
    (2), (4) Date: Dec. 5, 2000
(87) PCT Pub. No.: WO99/64559
    PCT Pub. Date: Dec. 16, 1999

(30) Foreign Application Priority Data

Jun. 8, 1998 (FR) .............................................. 98 07596

(51) Int. Cl.[7] .............................................. C12N 13/00
(52) U.S. Cl. ................................ 435/173.4; 435/287.1; 435/297.1; 435/297.5
(58) Field of Search ................. 435/285.2, 287.1, 435/297.1, 297.5, 173.4, 288.3; 204/403.01, 403.02, 403.03, 403.06

(56) References Cited

U.S. PATENT DOCUMENTS

| | | | |
|---|---|---|---|
| 5,759,846 A | 6/1998 | Stoppini et al. | 435/284.1 |
| 6,130,056 A | * 10/2000 | Correges | 435/29 |
| 6,303,082 B1 | * 10/2001 | John et al. | 422/68.1 |

FOREIGN PATENT DOCUMENTS

EP        0 689 051 A     12/1995

OTHER PUBLICATIONS

Database WPI, Section Ch, Week 8523, Derwent Publications Ltd., London, GB, AN 85–139721, XP002095669 & SU 1 124 022 A (AS USSR BIQEQUIP DE), Nov. 15, 1984.

* cited by examiner

Primary Examiner—David A. Redding
(74) Attorney, Agent, or Firm—Davis & Bujold, PLLC

(57) ABSTRACT

The invention concerns a device comprising a support (11) in the thickness of which is produced a supply chamber (12) with an inlet duct (13) for nutrient liquid and a discharge duct (14) for said liquid. A capsule (22) capable of receiving organic cells is provided on the support (11). The supply chamber (12) and the support (11) are separated by a porous membrane (16) comprising an array of electrodes (17) arranged so as to be in contact with different zones of the group of cells, thereby enabling their electrophysiological activity to be analyzed. The device enables to increase the life span of cells and to carry out analyses simply and without affecting the cell organization.

11 Claims, 2 Drawing Sheets

DEVICE FOR ORGANIC CELL CULTURE AND FOR STUDYING THEIR ELECTROPHYSIOLOGICAL ACTIVITY AND MEMBRANE USED IN SAID DEVICE

The present invention concerns a device for culturing a mass of organic cells and studying the electrophysiological activity of the cells, in which the cells are placed on at least one porous membrane, the lower surface of which contacts a liquid nutrient, said device comprising at least one electrode in contact with said mass of organic cells.

The present invention also concerns a membrane made of porous synthetic material and the use of said membrane to form a hemato-encephalic barrier.

BACKGROUND OF THE INVENTION

Various devices currently exist for measuring the electrophysiological activity of a mass of organic cells.

In particular, such a device is described in French Patent Application No. FR-A-2 733 055. This document describes a device for keeping tissue explants alive and for the monitoring and continuous analysis of the electrophysiological and biochemical activity of the tissue being studied. The device is formed of two half cards which form the upper and lower half, respectively, of the interface and which are assembled to form one card that can be inserted inside an electronic case designed specifically for this purpose.

This device gives satisfactory results, but it also has a certain number of disadvantages. The electrodes are actually forced toward the cells until they contact the cells. This injures a certain number of cells, shortening their life span. After a certain length of time, the electrodes and the cells become tightly attached to each other. When it is necessary to remove the cells, for example, to perform microscopic analysis, some of them remain attached to the electrodes, which destroys the structure of the cell mass and renders them useless.

In this device the cells are nourished from below and the electrodes are placed upon the cell mass. Thus, these electrodes block the tissues from view. It is important to be able to see the cells in order to determine how the tissues are organized and which electrodes should be used. Another reason is for controlling tissue survival.

In addition, the fact that the electrodes are placed on the cells prevents intervention on the tissues being analyzed. Furthermore, this means that the electrodes must possess a relatively high degree of mechanical resistance, since they are formed of copper tracks that do not rest on a substrate. Additionally, because the card is formed of two half-cards, a large number of pieces must be manufactured and assembled.

Since the electrodes are located between the two half-cards, one end of the electrode must be placed in an area that is accessible through an electrical connector. Since each card is a single-use card, the costs increase due to the number of pieces required and the complexity of the device.

Other devices with glass substrates have also been developed. In these devices, biological tissues must be attached in order to adhere to the substrate. Since the substrate is not porous, the device must be placed in a moving apparatus that successively submerges and lifts the tissue to allow respiration. This device is heavy and does not allow long-term survival once movement has stopped. Furthermore, it is difficult to make several substrates simultaneously on one plate. Making these substrates is an especially long and expensive process.

SUMMARY OF THE INVENTION

The present invention eliminates these disadvantages with an economical device made of a small number of pieces for electrophysiological and/or microscopic cell analysis with no cell destruction.

These goals are achieved using a device such as the device described in the preamble, characterized in that the electrodes are located on the porous membrane.

According to a preferred embodiment, the device comprises a network of electrodes.

Each electrode advantageously comprises an analysis zone which can be placed in contact with the cell mass and a measurement zone which can be placed in contact with an apparatus that either generates an electrical signal and/or measures an electrical signal.

The porous membrane is preferably maintained on a rigid support.

Said rigid support advantageously contains a liquid nutrient supply chamber which communicates with a liquid nutrient inlet duct and a liquid nutrient outlet duct and which has an opening communicating with said porous membrane.

According to a preferred embodiment, a capsule which maintains the organic cells in a controlled environment surmounts the porous membrane. This capsule may comprise a gas injection duct and a gas exhaust duct.

According to a particular embodiment of the invention, the electrode measurement zones in the electrode network are arranged in a circle.

The electrode network advantageously includes a position indexing means.

According to a preferred embodiment, the porous membrane is transparent.

The objectives of the invention are also achieved by a membrane such as the membrane described in the preamble, characterized in that it comprises at least one electrode placed upon said membrane.

According to a preferred embodiment, the membrane comprises a network of electrodes placed on said membrane.

According to a preferred embodiment, each electrode comprises at least one analysis zone, one measurement zone, and one connection zone.

Finally, the objectives of the invention are also achieved by a method of making a hemato-encephalic barrier model from a membrane such as that described above, said method characterized by the steps of treating the porous membrane so the endothelial cells will adhere to it, placing the endothelial cells on a surface of the porous membrane that does not have an electrode, cultivating said endothelial cells until a layer of cells has formed, and placing a slice of organotypical culture on the other surface of the porous membrane which has at least one electrode.

BRIEF DESCRIPTION OF THE DRAWINGS

The present invention will be better understood with reference to the description of a particular embodiment and to the attached drawings, in which.

DESCRIPTION OF THE PREFERRED EMBODIMENTS

Figure 1:
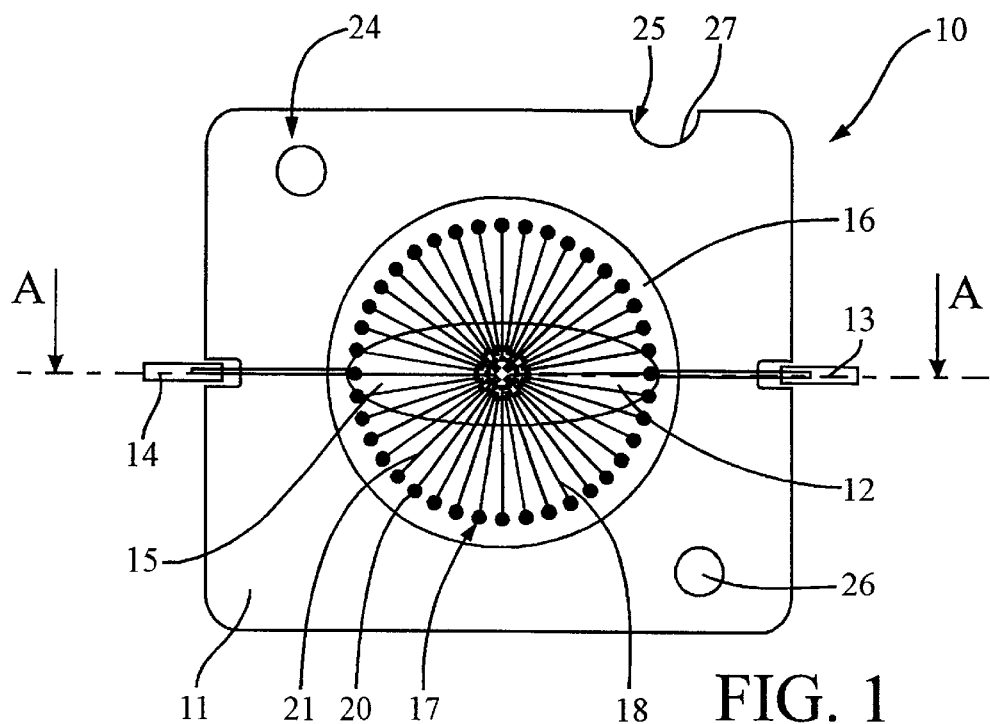
FIG. 1 is an overhead view of the device of the present invention.

With reference to the drawings, device 10 comprises a support 11 with a liquid nutrient supply chamber 12 formed in the wall. Said supply chamber communicates with an inlet duct 13 connected to a liquid nutrient perfusion system (not shown). This chamber also communicates with a liquid nutrient exhaust duct (14).

This chamber also comprises an opening 15 in the upper portion of the support. A transparent porous membrane 16 is placed on support 11 so as to cover opening 15. Said porous membrane 16 may be made of polyethylene terephthalate (PET) or particularly of polycarbonate. It comprises a network of electrodes 17 made directly on the membrane. Each electrode 18 of electrode network 17 comprises an analysis zone 19, a measurement zone 20, and a connection zone 21.

Analysis zone 19 is a non-insulated portion of the electrode. This zone is located above opening 15 in supply chamber 12. Measurement zone 20 is also a non-insulated portion of the electrode. It may be circular in shape with one surface that can easily be placed in contact with a connector.

Connection zone 21 is an insulated portion of the electrode, connecting analysis zone 19 to measurement zone 20.

The electrodes may be made of gold or platinum. The electrode network may be made according to several different methods. In one of these methods, a layer of gold is vaporized onto the porous membrane using a known method known as "plasma vapor deposition" (PVD) or by vacuum vaporizing. Next, a layer of photo resistant material is deposed. This layer is first printed through photographic mask reproducing the electrode network. The piece is then developed. The gold is machined chemically, then the membrane is rinsed before the first layer of photo resistant material has dissolved completely.

Insulating certain portions of the electrode network is done in the following way: a layer of a second photo resistant material is deposited on the membrane by dipping. The material is cooked, then another printing take place using a photographic mask reproducing the insulated electrode zones. Next, the membrane undergoes development and then rinsing.

The electrode network may also be made using the PVD gold vapor deposition process through a first mask. The insulating "network" is then deposed using a similar PVD method through a second mask. The insulation may be titanium oxide, for example.

Each electrode may also have a non-insulated zone constituting analysis zone 19, which may be square shaped. This non-insulated zone is located near the end of each electrode, above supply chamber opening 15. Gold or platinum is then deposed by electrodeposition in the non-insulated zone. This method is advantageous from different points of view. On the one hand, it provides good electrical contact between the cells and the electrodes. On the other hand, it decreases electrode impedance. Finally, it is particularly easy to modify the active electrode surface, that is the surface on the non-insulated zone. It is also possible to make electrodes with different active surfaces in the same electrode network.

In the embodiment illustrated, the electrode measurement zones are arranged in a circle so as to be easily accessible when activating the electrodes or measuring electrode signals. Obviously, other configurations also could have been chosen.

Device 10 further comprises a capsule 22 formed of a lateral wall and a partially open base. Said capsule is rigidly affixed above the porous membrane so that supply chamber opening 15 can communicate with the opening at the base of capsule 22 through porous membrane 16.

Said capsule 22 further comprises a cover 23 that can be placed on the capsule to protect its contents from the exterior environment. This cover can be hermetically sealed. The capsule may also comprise a gas injection duct 28 and a gas exhaust duct 29. Depending upon the measurements to be taken or the nature of the cells or products to be tested, a gas may be introduced through this gas injection duct. It is also possible to generate gas flow in the chamber by introducing a gas through the injection duct and evacuating it through the gas exhaust duct.

Support 11 is rigid and it comprises a support means 24 and position indexing elements 25. Support means 24 may consist of two holes 26 cooperating with two pins on a connection box (not shown). Said support means maintain device 10 in position within the connection box.

The indexing means 25 may consist, for example, of a notch 27 cooperating with a prong (not shown) on the connection box. They ensure that the device is correctly positioned in the connection box and more particularly, that it is not placed in a position that is symmetrical relative to the correct position.

Figure 2:
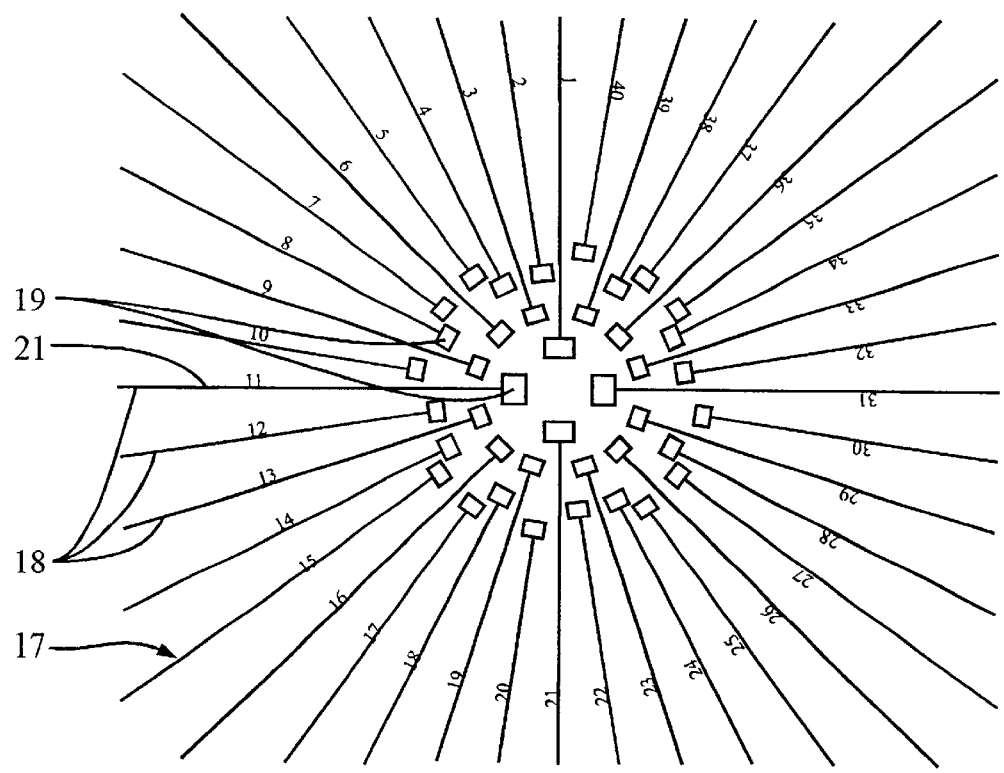
FIG. 2 is an enlargement of a portion of the device of FIG. 1.
Figure 3:
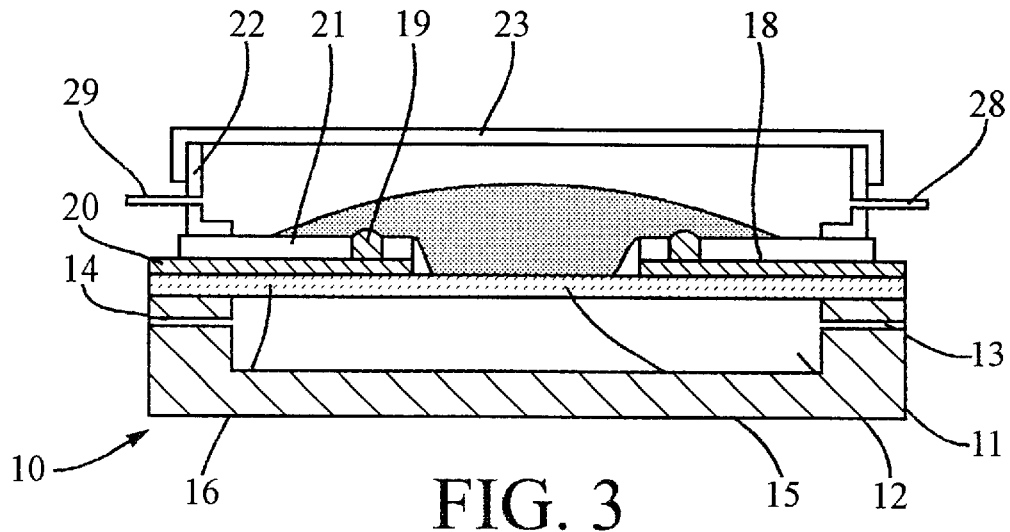
FIG. 3 is a cross-section taken along line A—A of FIG. 1.

When the device is in use as shown in FIGS. 1 through 3, a cellular mass is placed in capsule 22. The mass may be placed directly on porous membrane 16, in the conventional manner. However, it is also possible to cultivate cells on a porous membrane that is circular, for example, and then place these cells along with the circular membrane into the capsule. This is particularly useful in situations where cells must be cultivated before it is possible to proceed with analysis. In this way it is possible to stimulate and record the cells' electrophysiological responses through the precut membrane, without the biological tissue coming into direct contact with the electrodes.

A liquid nutrient flows into supply chamber 12 through inlet duct 13. This liquid comes into contact with the porous membrane and completely covers the cellular mass of liquid nutrient with a film of culture medium. This permits a thorough diffusion of the gases throughout the cell and ensures cell longevity. Furthermore, it eliminates the need to move the entire device, as with certain prior art devices. Cover 23 on capsule 22 is generally kept closed to avoid pollutants from the exterior environment.

The film of liquid nutrient also presses the cell mass against the electrodes, ensuring strong electrical contact between the electrodes and the cells, making it unnecessary to attach these cells.

The device is advantageously placed in a connection box (not shown) which connects each of the measurement zones on the electrodes to an input on the connection box. This allows an electric signal to be simply transmitted to one or more selected electrodes on the electrode network, while introducing said signal to the corresponding input or inputs on the connection box.

Likewise, it allows the simple measurement of an electrical signal from one or more electrodes in the electrode network.

Inlet ducts 13 and exhaust ducts 14 allow the introduction of chemical substances to be tested while the device still remains in the environment in which the electrical measurements are performed.

Since the porous membrane is transparent, the cell mass can be microscopically analyzed without the need of removing the electrodes and thereby destroying its structure. The membrane can also be removed from the support, facilitating manipulation during various tests.

Figure 4:
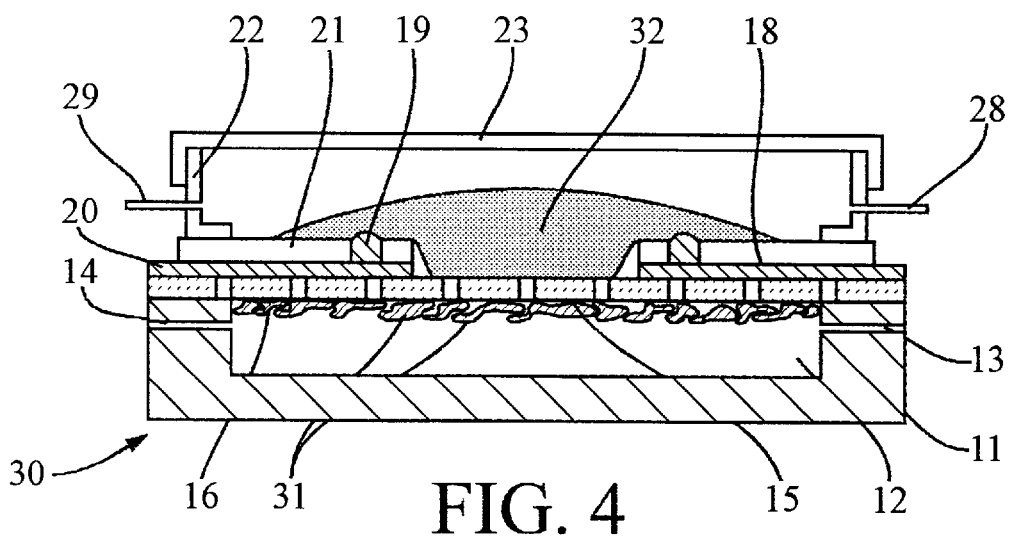
FIG. 4 is a cross-section showing a specialized use of the device of the invention.

FIG. 4 shows a particular use of device 30 of the invention, in which a model of a hemato-encephalic barrier has been constructed. This hemato-encephalic barrier is formed of endothelial cells which carpet the capillaries of the central nervous system. These cells have specialized properties compared to cells from other organs. They form a barrier that prevents the passage of most hydrosoluble molecules except those which have a particular transporter, such as glucose, for example.

This barrier plays an important role in the protection of nerve tissue. It sometimes blocks passage of certain medications which are active, but cannot pass through the barrier. For this reason, it is important to construct hemato-encephalic barrier models to test the permeability of new medications.

The hemato-encephalic barrier model developed with the device of the present invention is obtained through the co-culture of endothelial cells 31 and slices of organotypical cells 32. This barrier model is particularly interesting because it discloses molecular permeability and its effects on nerve tissue in a single experiment.

As shown in detail in FIG. 4, the co-culture of endothelial cells 31 and organotypical cells 32 is integrated with porous membrane 16. The unit thus formed tests molecular permeability in a model that is very close to the in vivo situation, but considerably simpler and more economical.

In this embodiment, porous membrane 16 is first treated so endothelial cells 31 will adhere to it. Some endothelial cells are then injected into the chamber. When they form a compact layer, an organotypical culture 32 is placed on the other side of the membrane, on electrodes 18 forming the electrode network. The entire unit is kept in an incubator for several days, the length of time required for the hemato-encephalic barrier to form. The device of the invention, to which the hemato-encephalic barrier has been added, is used as previously described. The molecules to be tested are injected into the chamber through inlet duct 13.

The permeability of the neuroactive molecules can be determined directly by analyzing modifications in electrophysiological activity in the nerve tissue, which modifications will be apparent due to the presence of molecules to be tested in the tissues. The electrode network stimulates and simultaneously records electrical activity in the nerve tissue using an appropriate processing device.

The device of the present invention is generally a single-use device. It is discarded after each analysis. The number of pieces involved has been reduced to a minimum. This reduces the cost of the device.

Furthermore, because a flexible substrate is used, it is easy to make several substrates simultaneously on a plate and then cut away the plate when the electrodes have been made. This allows the substrates to be manufactured industrially.

The present invention is not limited to the embodiment described, but extends to all variations that are obvious to one skilled in the art. Specifically, the shape of porous membrane 16 need not be circular. If a square shaped membrane were used, for example, then positioning the sides of the square would ensure positioning of the electrodes. This positioning can be important when the device must cooperate with a connection box having connectors in fixed positions.

What is claimed is:

1. A device for the culture of a mass of organic cells and for analyzing the electrophysiological activity of said cells, comprising:

at least one porous membrane, the cells being placed on said at least one porous membrane, the lower surface thereof being in contact with a liquid nutrient, electrodes which are in contact with said mass of organic cells, wherein the electrodes (18) constitute a network (17) of electrodes which is provided on the porous membrane (16), each electrode (18) having an analysis zone (19) being placed in contact with the cells mass, including a measurement zone (20) being placed in contact with an apparatus generating an electrical signal or measuring an electrical signal and a connection zone (21) being an insulated portion of the electrode (18) connecting analysis zone (19) to measurement zone (20).

2. A device according to claim 1, wherein the porous membrane (16) is held by a rigid support (11).

3. A device according to claim 2, wherein the rigid support (11) contains a liquid nutrient supply chamber (12), said chamber communicating with a liquid nutrient inlet duct (13) and a liquid nutrient exhaust duct (14) and having an opening (15) which communicates with said porous membrane (16).

4. A device according to claim 1, wherein a capsule (22) surmounts the porous membrane (16) for providing for the organic cells mass a controlled environment.

5. A device according to claim 4, wherein the capsule (22) is provided with a gas injection duct (26) and with a gas exhaust duct (29).

6. A device according to claim 1, wherein the measurement zones (20) of the electrodes (18) in the electrode network (17) are arranged in a circle.

7. A device according to claim 1, wherein the electrode network (17) comprises a position indexing means (25).

8. A device according to claim 1, wherein the porous membrane (16) is transparent.

9. A method of making a hemato-encephalic barrier model from a porous membrane made of synthetic porous material, wherein the porous membrane comprises:

a plurality of electrodes supported on the porous membrane wherein the electrodes (18) constitute a network (17) of electrodes;

each electrode (18) having an analysis zone (19) placed in contact with a mass of cells;

a measurement zone (20) of each electrode (18) being placed in contact with an apparatus generating an electrical signal or measuring an electrical signal; and a connection zone (21) of each electrode (18) being an insulated portion of the electrode (18) connecting analysis zone (19) to measurement zone (20);

wherein the method comprises the steps of:

treating the porous membrane (16) so the cells (31) will adhere to the porous membrane (16);

placing the cells (31) on an area of the porous membrane (16) which does not support any electrode;

cultivating said cells (31) until said cells (31) form a layer; and placing a slice of an organotypical culture (32) on the other surface of the porous membrane (16) which has at least one electrode.

10. A method of assessing permeability of neuroactive molecules through a transparent membrane with a device for culture of a mass of organic cells and for analyzing electrophysiological activity of the cells, the device comprising:

a blood-brain barrier model at least one transparent membrane, the cells being placed on the at least one membrane, a lower surface of the at least one membrane being in contact with a liquid nutrient; and electrodes which are in contact with the mass of organic cells, the electrodes (18) constituting a network (17) of electrodes which is provided on the membrane (16), each electrode (18) having an analysis zone (19) placed in contact with the mass of organic cells, including a measurement zone (20) of each electrode (18) being placed in contact with an apparatus generating an electrical signal or measuring an electrical signal and a connection zone (21) of each electrode (18) being an insulated portion of the electrode (18) connecting analysis zone (19) to measurement zone (20);

wherein the method comprises the steps of:

treating the membrane (16) so the organic cells will adhere to the membrane (16);

placing the organic cells (31) on an area of the membrane (16) which does not support any electrode;

cultivating the organic cells (31) until the organic cells (31) form a layer; and placing a slice of an organotypical culture (32) on the other surface of the membrane (16) which has at least one electrode.

11. A method according to claim 10, further comprising the step of using a blood-brain barrier as the membrane (16).

* * * * *